(12) United States Patent
Hanina

(10) Patent No.: US 11,484,240 B2
(45) Date of Patent: Nov. 1, 2022

(54) MODIFICATION OF BEHAVIOR OR PHYSICAL CHARACTERISTICS THROUGH VISUAL STIMULATION

(71) Applicant: VDynamics LLC, New York, NY (US)

(72) Inventor: Adam Hanina, New York, NY (US)

(*) Notice: Subject to any disclaimer, the term of this patent is extended or adjusted under 35 U.S.C. 154(b) by 41 days.

(21) Appl. No.: 16/926,814

(22) Filed: Jul. 13, 2020

(65) Prior Publication Data

US 2020/0337577 A1 Oct. 29, 2020

Related U.S. Application Data

(63) Continuation of application No. 15/475,723, filed on Mar. 31, 2017, now Pat. No. 10,736,526.

(Continued)

(51) Int. Cl.
*A61B 5/0205* (2006.01)
*A61B 5/318* (2021.01)
*G06Q 30/02* (2012.01)
*A61B 3/032* (2006.01)
*G06Q 50/00* (2012.01)

(Continued)

(52) U.S. Cl.
CPC .............. *A61B 5/318* (2021.01); *A61B 3/032* (2013.01); *A61B 5/369* (2021.01); *G06Q 30/02* (2013.01); *G06Q 50/00* (2013.01); *G06V 40/166* (2022.01); *A61B 3/113* (2013.01); *A61B 5/021* (2013.01); *A61B 5/02438* (2013.01); *A61B 5/1114* (2013.01); *A61B 5/165* (2013.01)

(58) Field of Classification Search
None
See application file for complete search history.

(56) References Cited

U.S. PATENT DOCUMENTS 5,027,208 A * 6/1991 Dwyer, Jr .............. H04N 5/278
348/516
6,516,464 B1 * 2/2003 Claessens .............. H04H 60/46
725/10

(Continued)

OTHER PUBLICATIONS

Johan C. Karremans et al., "Beyond Vicary's fantasies: The impact of subliminal priming and brand choice," Journal of Experimental Social Psychology, vol. 42, pp. 792-798 (2006).
Kaede Kido et al., "Serial order learning of subliminal visual stimuli: evidence of multistage learning," Frontiers in Psychology, vol. 6, Article 76 (Feb. 2015).

(Continued)

*Primary Examiner* — Christopher G Findley
(74) *Attorney, Agent, or Firm* — Steptoe & Johnson LLP; Carl B. Wischhusen

(57) ABSTRACT

A system and a process are provided for evaluating subliminal pixel patterns and identifying trigger patterns, which are pixel patterns that trigger a response in subjects exposed to the pattern. Each pixel pattern is embedded in a digital video or a digital still image. Pixel patterns that are found to induce reactions in subjects are identified as trigger patterns and are flagged for re-testing. Re-tested trigger patterns that repeatably induce reactions are identified as positive trigger patterns and are studied further. Variations are made to a positive trigger pattern to determine whether small changes can affect how a subject responds when exposed to that positive trigger pattern. A positive trigger pattern is evaluated to determine whether it can induce an emotional, a physical, and/or a behavioral change in the subjects and, if so, the positive trigger pattern is applied to a real-world situation.

20 Claims, 5 Drawing Sheets

Related U.S. Application Data

(60) Provisional application No. 62/316,069, filed on Mar. 31, 2016.

(51) Int. Cl.
  *A61B 5/369*    (2021.01)
  *G06V 40/16*    (2022.01)
  *A61B 3/113*    (2006.01)
  *A61B 5/021*    (2006.01)
  *A61B 5/11*     (2006.01)
  *A61B 5/024*    (2006.01)
  *A61B 5/16*     (2006.01)

(56) References Cited

U.S. PATENT DOCUMENTS

| | | | |
|---|---|---|---|
| 2002/0107454 A1* | 8/2002 | Collura | G16H 40/67 600/544 |
| 2003/0125634 A1* | 7/2003 | Eda | A61B 5/16 600/544 |
| 2011/0002512 A1 | 1/2011 | Uehara et al. | |
| 2016/0345060 A1 | 11/2016 | Marci et al. | |

OTHER PUBLICATIONS

William Raft Kunst-Wilson et al., "Affective Discrimination of Stimuli That Cannot be Recognized," Science, vol. 27, pp. 557-558 (Feb. 1980).

Holger F. Sperdin et al., "Submillisecond Unmasked Subliminal Visual Stimuli Evoke Electrical Brain Responses," Human Brain Mapping, vol. 36, pp. 1470-14833 (2015).

\* cited by examiner

MODIFICATION OF BEHAVIOR OR PHYSICAL CHARACTERISTICS THROUGH VISUAL STIMULATION

CROSS-REFERENCE TO RELATED APPLICATION(S)

The application is a continuation of U.S. patent application Ser. No. 15/475,723, filed Mar. 31, 2017, the entire contents of which is incorporated herein by reference. This application also claims the benefit of priority of U.S. Provisional Application No. 62/316,069, filed on Mar. 31, 2016, the entire contents of which is incorporated herein by reference.

FIELD OF THE INVENTION

The present invention relates to methods and systems for identifying subliminal signals that are effective for causing a physical reaction and/or an emotional reaction in subjects exposed to the subliminal signals, for determining a type or types of behavioral changes and/or physical changes that may be brought about by exposing subjects to the subliminal signals, and for utilizing the subliminal signals to induce a desired action in subjects exposed to the subliminal signals.

RELATED ART

Subliminal messaging or perception relates to the perception of data or information subconsciously. That is, subjects exposed to the data or information are not aware of its existence, i.e., it cannot be perceived consciously. The data or information, however, is perceived by the subjects on a subconscious level, i.e., the subjects react to the data or information but are unaware that the data or information has been registered by their brains. For example, the placement of a can of Coke® on a table in a scene of a movie would not be considered a subliminal message, because the can of Coke® is clearly visible and able to be perceived as a can of Coke® by viewers. On the other hand, if a can of Coke® is inserted only in a few frames of the movie but the can of Coke® is not perceptible, i.e., the viewers do not know that a can of Coke® has appeared during the movie, then the can of Coke® can be considered a subliminal message. The subliminal appearance of the can of Coke®, however, does not necessarily produce a reaction in the viewers and, even if a reaction is produced, the reaction may not be an intended reaction.

Subliminal messaging or perception has in the past been associated with corporate manipulation of consumers, in which purchasing behavior is influenced by suggestive text or pictures inserted into movies. The suggestive text or pictures cannot be perceived consciously but purportedly were used for behavior control.

Although there has been concern regarding misuse of subliminal perception, the effectiveness of subliminal perception for mind control or behavior control has been questioned and has not been firmly established. James Vicary claimed in 1957 that by flashing short advertisements during a movie, urging viewers to eat popcorn and drink Coca-Cola®, sales of these items increased by over 57% and 18%, respectively. Vicary could not reproduce his experimental findings, however, and he later retracted the original claim. More recently, a 2015 study (H. Sperdin et al., "Submillisecond unmasked subliminal visual stimuli evoke electrical brain responses," Human Brain Mapping, vol. 36, no. 4, pp. 1470-1483, April 2015) reports evidence of induced brain activity when a subject was exposed to a subliminal visual stimulus. In this study, the subject was monitored using electroencephalography (EEG) techniques while being exposed to a subliminal checkerboard pattern. It was found that the subliminal checkerboard pattern induced brain activity, and the onset of the induced brain activity occurred at a flash duration of about 250 µs. It was also found that the induced brain activity for the subliminal checkerboard pattern was localized to a particular region of the brain. Although this 2015 study appears to indicate that subliminal perception can cause a physical reaction and/or a mental reaction in a subject, i.e., can induce brain activity in a subject, whether the reaction(s) can bring about a change in the behavior of the subject or a change in a physical characteristic of the subject has not been explored.

SUMMARY

According to a first embodiment of the present invention, a system and a process are provided for evaluating subliminal pixel patterns and identifying trigger patterns, which are pixel patterns that trigger a response in subjects exposed to the pattern. Each pixel pattern is embedded in a digital video or a digital still image. Pixel patterns that are found to induce reactions in subjects are flagged for re-testing. Re-tested trigger patterns that repeatably induce reactions are identified as "positive trigger patterns" and are studied further.

According to a second embodiment of the present invention, a system and a process are provided for evaluating whether a variation in a positive trigger pattern can affect how a subject responds when exposed to that positive trigger pattern. Variations are made to the positive trigger pattern and/or to imagery in which the positive trigger pattern is embedded to determine whether the positive trigger pattern is robust enough to induce a reaction in the subjects even if it is changed and, if so, to determine how much the positive trigger pattern may be changed and still induce a reaction in the subjects. Variations in the positive trigger pattern that induce a reaction in the subjects are identified as "positive variations."

According to a third embodiment of the present invention, a system and a process are provided for determining a type of reaction, or types of reactions, if any, induced in a subject exposed to a positive trigger pattern and its associated positive variations (collectively referred to as "positive patterns" herein). That is, subjects are exposed to the positive patterns to determine whether the induced reaction can bring about emotional, physical, and/or behavioral changes in the subjects. Positive patterns that are found to cause emotional, physical, and/or behavioral changes in the subjects are identified as "effective subliminal patterns."

According to a fourth embodiment of the present invention, a system and a process are provided for utilizing an effective subliminal pattern to affect an emotional state, a physical state, and/or a behavioral state of viewers. Unlike the subjects in the previous embodiments, who are observed or monitored under testing conditions, the viewers in the present embodiment are exposed to the effective subliminal pattern under everyday settings or "real world" conditions.

BRIEF DESCRIPTION OF THE DRAWINGS

The features and advantages of the present invention will become more apparent from the detailed description set forth below when considered in conjunction with the attached drawings, in which like reference numbers indicate identical or functionally similar elements, of which.

DESCRIPTION OF THE INVENTION

Figure 1A:
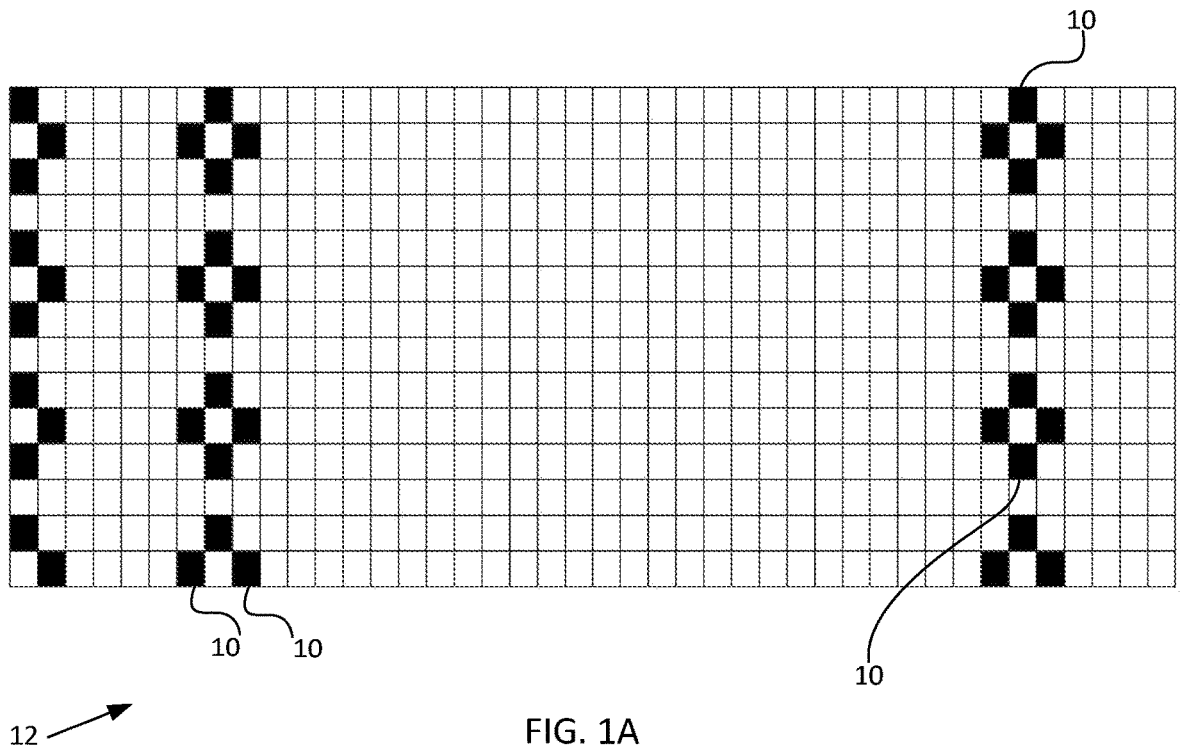
FIGS. 1A-1D schematically show examples of test patterns.
Figure 1B:
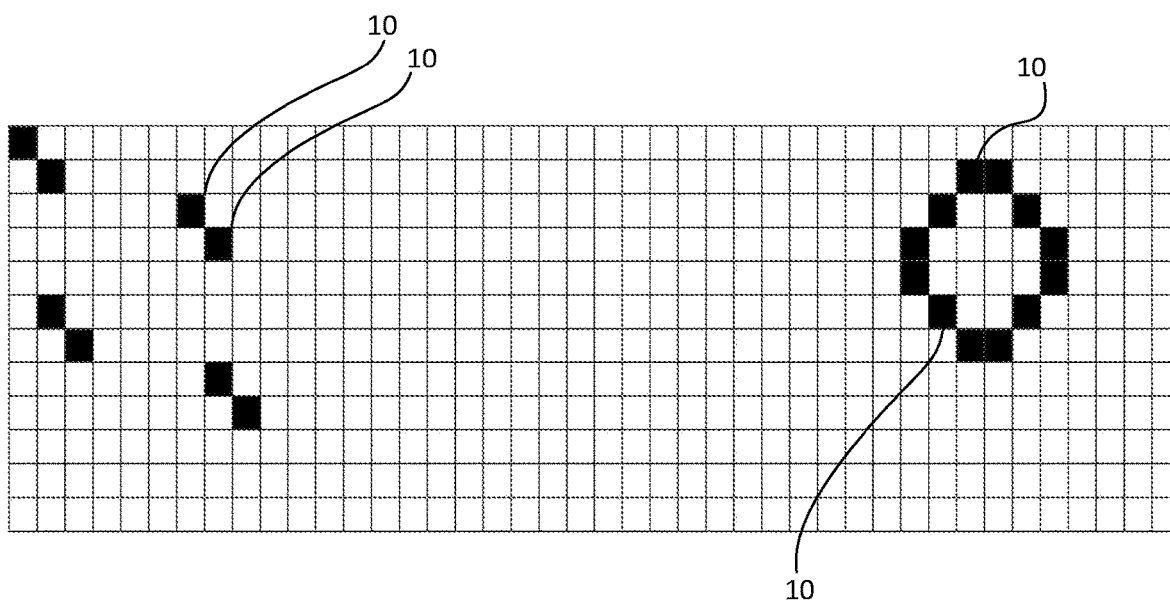
Figure 1C:
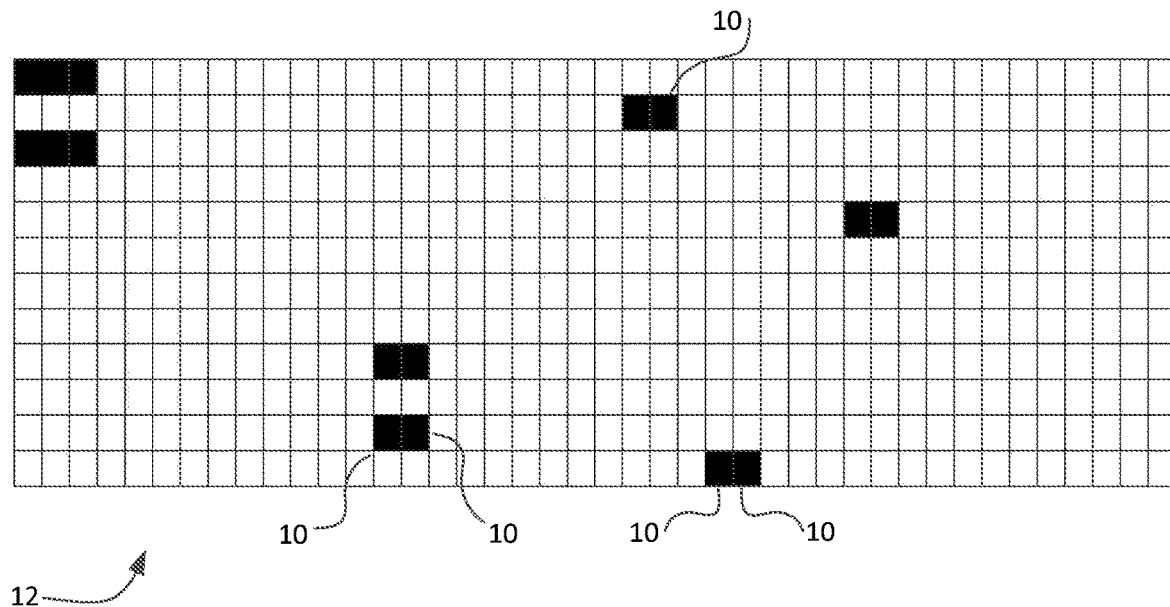
Figure 1D:
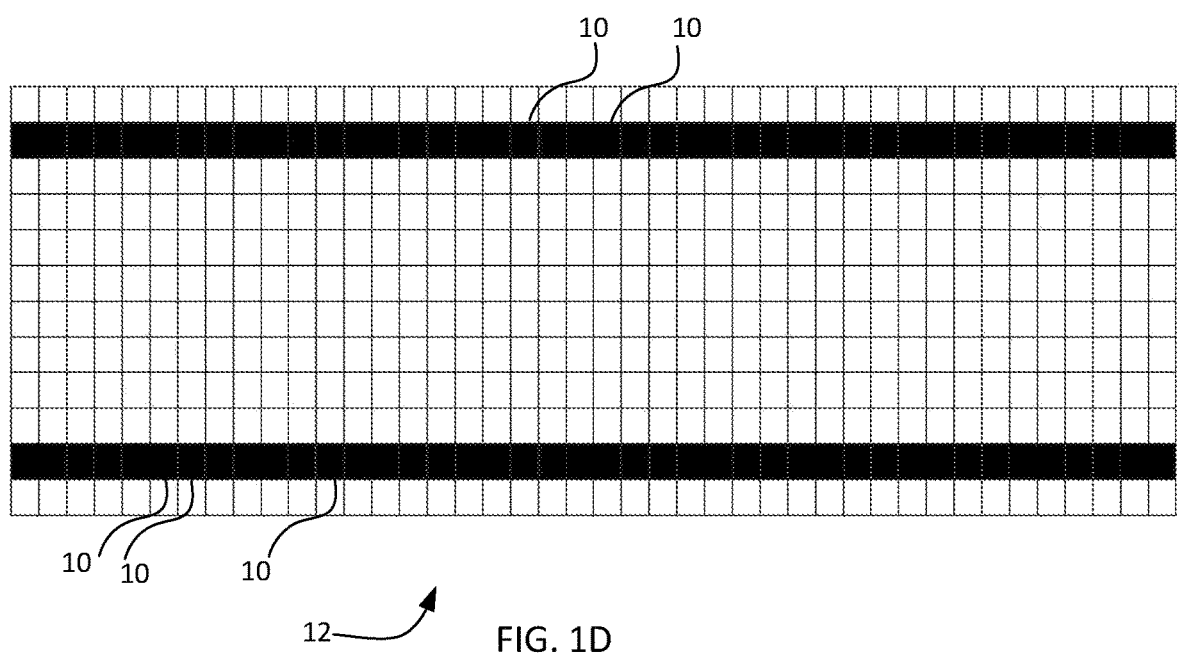

Aspects of the present invention provide an interface for affecting cognition or neural processing. Visual stimulation is used to bypass typical neural processing. Information is presented visually to a user (or viewer), and the information triggers neural stimulation that affects cognition. One or more types of visual information may be used to cause constructive or positive cognition, in which the viewer feels an increase in a characteristic (e.g., feels an increase in happiness) after being exposed to the visual information. One or more other types of visual information may be used to cause destructive or negative cognition, in which the viewer feels a decrease in a characteristic (e.g., feels a decrease in pain) after being exposed to the visual information. In the latter example, the negative cognition counteracts traditional cognition of pain, resulting in the viewer feeling less pain. In another example, gait or movement patterns may be affected or changed by using destructive or negative cognition to counteract typical neural processing or cognition.

First Embodiment

According to a first embodiment of the present invention, a system and a process are provided for evaluating subliminal pixel patterns and identifying trigger patterns, which are pixel patterns that trigger a response in subjects exposed to digital media (e.g., a digital video, a digital still image, and the like) containing the pixel patterns.

For example, a digital video is modified so that for a series of frames of the video a test pattern of pixels is changed to a predetermined color. The pixels of the test pattern need not be contiguous with one another, nor do the pixels of the test pattern need to appear in a repeated array. The test pattern is subliminal and cannot be discerned by the subjects when viewing the video. That is, the series of frames of the video containing the test pattern cannot be consciously identified by the subjects viewing the video.

Examples of test patterns, i.e., pixel patterns that may be tested, are shown in FIGS. 1A-1D. In FIGS. 1A-1D, pattern pixels 10 are embedded in the other pixels of the video frame, and are in one or more predetermined color(s) forming a test pattern 12. For example, the pattern pixels 10 overlay or replace the original pixels at the positions of the pattern pixels 10, so that when the video is shown the pattern pixels are shown as part of the video frame. The pattern pixels 10 may be randomly distributed (e.g., FIG. 1C) or may be arranged in a repeating pattern (e.g., FIG. 1A). Of course, other pixel patterns not specifically shown also may be tested and are within the scope of the present invention.

During exposure to the video, the subjects are monitored to see whether there is a reaction that occurs when the test pattern of pixels appears. If a reaction is observed in at least one of the subjects, the test pattern is identified as positive or a trigger pattern and flagged for further studies. If no reaction is observed in any of the subjects, the test pattern is identified as negative and not studied further.

The video with a flagged test pattern (i.e., a trigger pattern) is shown to the same subjects or to new subjects to confirm whether exposure to the trigger pattern can repeatably induce a reaction in at least one of the subjects. If repeatability cannot be confirmed for a predetermined percentage of exposures to the flagged test pattern (e.g., 25% or greater, 30% or greater, 40% or greater, 50% or greater), the flagged test pattern is identified as negative and not studied further. If repeatability is found, the flagged test pattern is identified as a positive trigger pattern to be studied further, as discussed herein in connection with the second embodiment of the present invention.

The subjects may be shown or exposed to the video collectively, such as in a room where all the subjects watch the video together on a single display screen, or the subjects may watch the video individually using a personal electronic device, such as by using a computer, a tablet, a smartphone, a head-mounted display device, a Google Glass™ device, or the like, to stream or access the video via an Internet link. Optionally, instead of using an Internet link, the video may be stored as video data on a computer-readable storage medium and displayed on a display screen directly using a display application of the personal electronic device.

The monitoring of the subjects during exposure to the video may occur in any one or a combination of ways.

Figure 2:
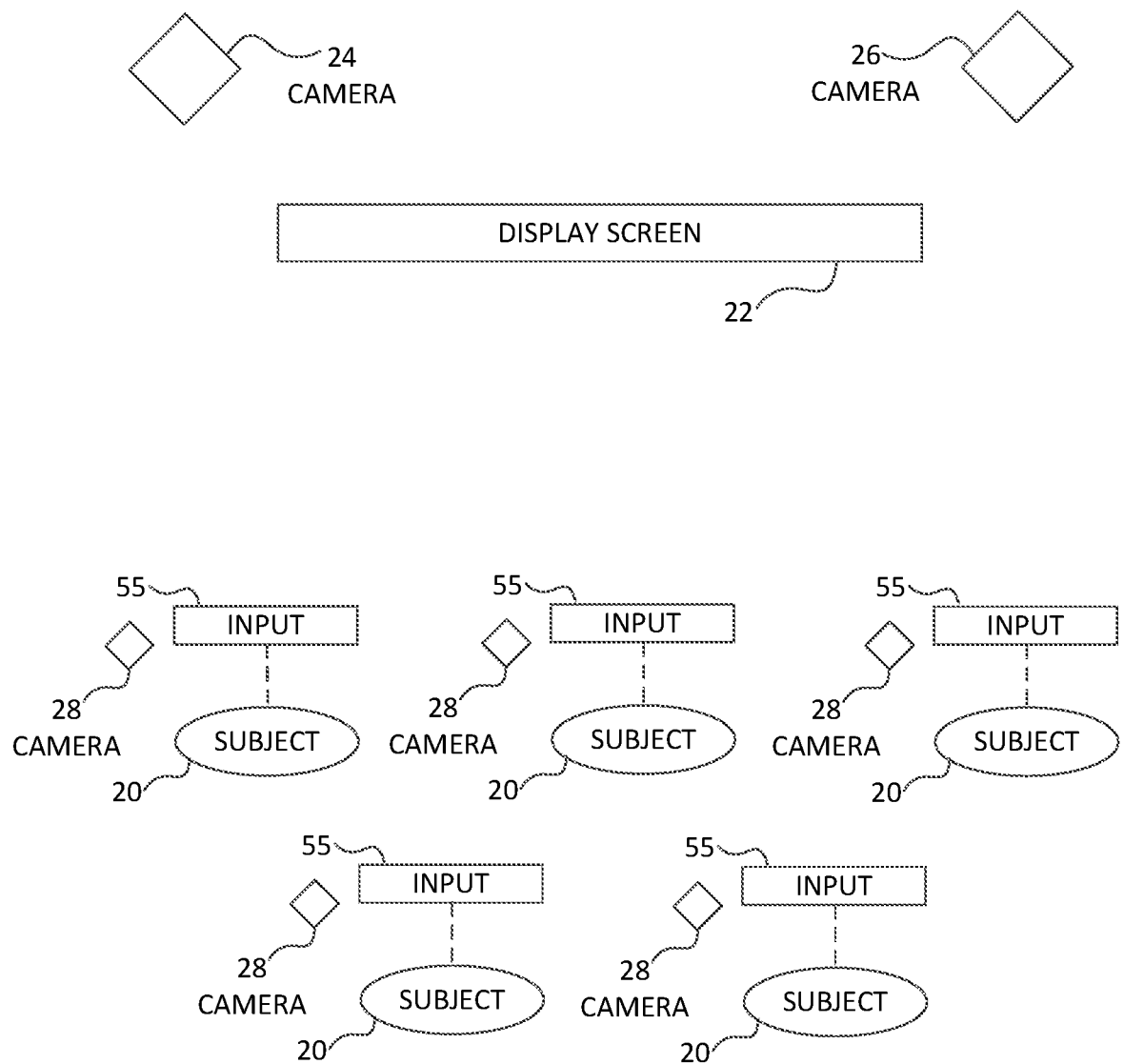
FIG. 2 schematically shows an arrangement for testing test patterns.

FIG. 2 schematically shows subjects 20 together in, for example, an auditorium. A display screen 22 is positioned so that the subjects 20 may all watch the video at the same time. The subjects 20 may be monitored using a video camera 24 or 26 or a group of video cameras 24 and 26 recording the subjects 20 during exposure to the video. Timestamps may be used to synchronize the occurrence of the test pattern in the video with the recording(s) of the subjects 20 shown or exposed to the video, so that the point(s) in the recording(s) of the subjects 20 at which the test pattern occurs is known. For example, if a single video camera 24 or 26 is used, the camera 24 or 26 may be arranged to capture the faces of the subjects 20. In another example, if multiple video cameras 24 and 26 are used, the cameras 24 and 26 may be arranged to capture different features of the subjects 20, such as the faces, the legs, the torsos, etc. Optionally, individual cameras 28 may be used to capture a particular feature or particular features of only one or only a few of the subjects 20, or each of the subjects 20 individually.

Figure 3:
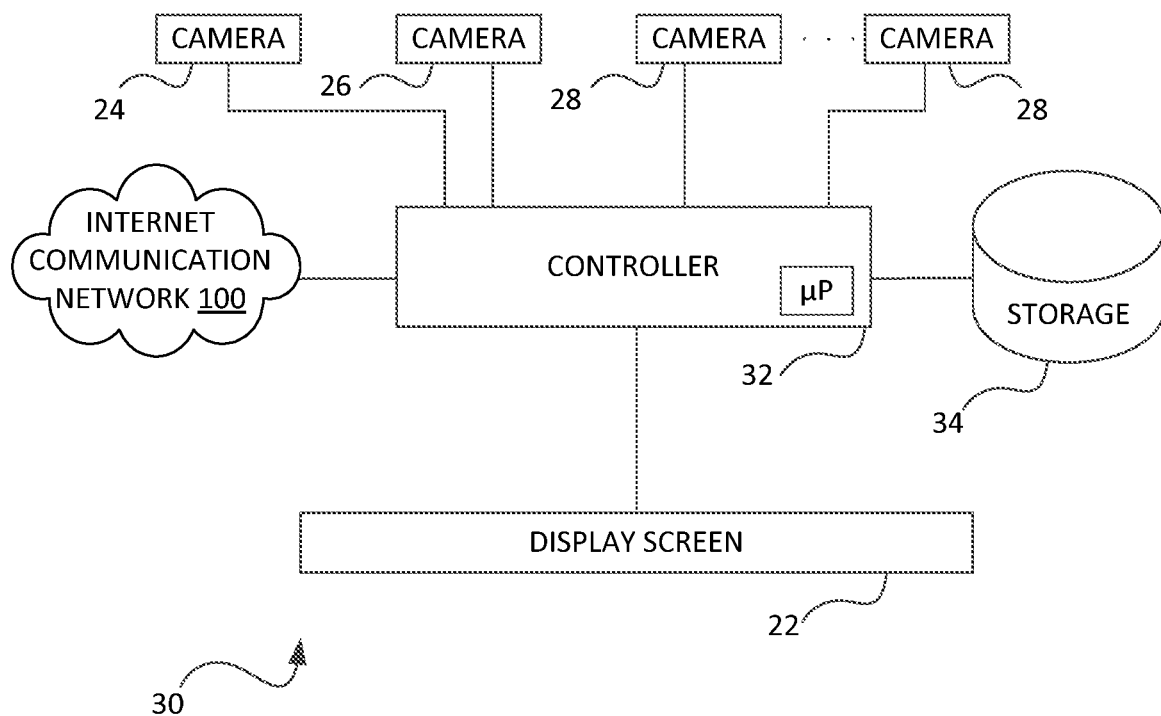
FIG. 3 schematically shows a system according to an embodiment of the invention.

FIG. 3 schematically shows a system 30 for implementing the aspect of the first embodiment shown in FIG. 2. A controller 32 includes a processor (not shown) programmed to control the displaying of the video on the display screen 22 as well as communications with the video cameras 24, 26, 28. Recordings made by the video cameras 24, 26, 28 are received by the controller 32 and stored in a storage device 34. The controller 32 provides timestamps for the recordings, so that the occurrence or occurrences of the test pattern can be associated with a particular section or sections of the recordings. This enables actions by the subjects 20 while watching the video to be correlated to the occurrence(s) of the test pattern in the video. Although FIG. 3 shows a physical connection between the controller 32 and other parts of the system 30, communications between the controller 32 and the other parts of the system 30 may take place wirelessly using wireless communication techniques known in the art.

Figure 4:
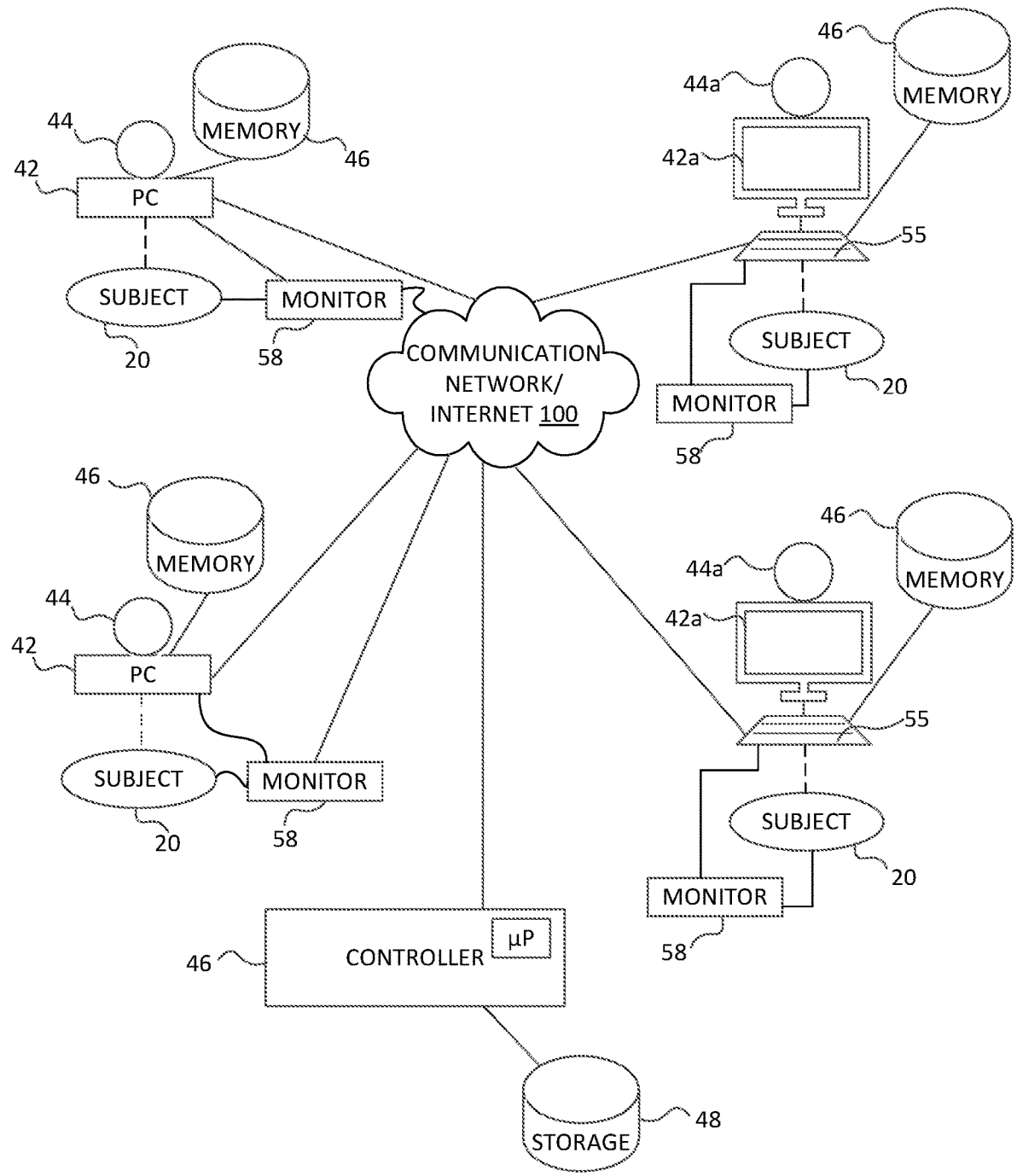
FIG. 4 schematically shows another system according to an embodiment of the invention.

If a subject 20 watches the video on a display screen of a personal electronic device 42 separately from another subject 20, each subject 20 may be monitored using a video camera 44 connected to the Internet 100 and/or to a storage device 46, or using a webcam 44a integrated into the personal electronic device 42 and connected to the Internet 100 and/or to the storage device 46, as schematically shown in FIG. 4. For example, if the webcam 44a or the video camera 44 is connected to the Internet 100, a video image of the subject 20 may be transmitted directly to a controller 46 at an external facility for storage in a storage device 48 for later analysis. Alternatively, or in addition to directly transmitting the video image to the external facility, the video image may be stored locally by the subject 20 on the storage device 46 for later analysis.

The storage devices 34, 46 may be any memory circuitry that is able to store image data, such as a hard-drive memory (e.g., solid-state-memory drive, optical-disk drive, etc.), a removable storage medium (e.g., flash/USB memory, optical disk, floppy disk, magnetic memory, etc.), and the like.

Physical characteristics of the subjects may also be monitored by a monitoring device 58 in addition or alternative to monitoring by webcam or video camera. For example, the heartrate of a subject when watching the video to can be monitored by an electrocardiogram (EKG) machine or by a specialized wristband equipped with a heartrate sensor, the pulse rate of a subject can be measured by a specialized wristband equipped with a pulse monitor, the blood pressure of a subject can be monitored by a blood pressure monitor, and the brain activity of a subject can be monitored by neuroimaging using an EEG machine, a magnetic resonance imaging (MRI) machine, or the like. Other physical characteristics not specifically identified above may also be monitored by devices and equipment known in the art, to determine whether changes occur in those characteristics as a result of exposure to the subliminal test pattern in the video.

With respect to monitoring by a recording a subject's face, known facial-recognition techniques may be used to detect movement in a facial feature. For example, an eye movement, a brow movement, a mouth movement, a change in pupil size, etc., may be detected using facial-recognition software. During analysis of the recording, detected facial movements that are found to occur while the test pattern is being shown, or shortly afterwards, may be used to signify reactions induced by the test pattern, and to indicate that the test pattern should be flagged for further studies.

Similarly, with respect to monitoring a physical characteristic such as the heartrate, the pulse rate, the blood pressure, the brain activity, or any other physical characteristic, an electronic datafile or recording is made of data collected while a subject is watching the video. A baseline reading is established from the recording for when the subject is watching the video without the test pattern. If a deviation or change from the baseline reading is found to occur in the recording, corresponding to when the test pattern appears in the video, then the video is flagged for further studies. That is, the coincidental timing of the deviation and the occurrence of the test pattern is taken to be an indication that the test pattern induced a reaction in the subject.

The monitoring discussed above is passive monitoring requiring no deliberate input by the subjects. Active monitoring may also be used in addition to or instead of passive monitoring. In active monitoring, the subjects are asked to activate an input device when the video causes them to have a reaction. The reaction may be specified to be a particular emotion such as happiness, sadness, anger, nervousness, anxiety, etc., a particular physical condition such as pain, tear production, change in breathing rate, etc., or the reaction may be general such as a change in how the subject feels.

For example, the subjects 20 may be provided with an input device 45, such as a touchpad, and instructed to tap on the touchpad every time they have a reaction while watching the video. If the timing of the taps occurs coincidentally with when the test pattern appears on the video, then the test pattern is flagged for further studies. Optionally, instead of a touchpad, the input device 55 may be a keyboard, a mouse, or any electronic device that the subjects 20 may use to send a signal to a processor. The processor registers the inputted signals and if the signals correspond to when the test pattern appears in the video, then the video is flagged for further studies.

Similar to the discussion above, if the monitoring devices for monitoring the physical characteristics of the subjects are connected to the Internet, monitoring data may be transmitted directly to an external facility for storage for later analysis. Alternatively, or in addition to directly transmitting the data to the external facility, the data may be stored in storage devices local to the subjects, for later analysis.

A plurality of videos with test patterns may be evaluated. The test patterns may occur sequentially in the same video, or may be embedded in separate videos. Each test pattern is subliminal so that it appears for a duration that is sufficiently short that it cannot be consciously noticed by the subjects viewing the video.

For example, the video may have a monochrome green background in which a test pattern of black pixels appears subliminally in a series of frames of the video. The test pattern may be repeated in the video sporadically at random intervals or periodically at known intervals. The same test pattern may be evaluated for videos showing monochrome backgrounds of different colors and/or with the test pattern having non-black pixels.

Optionally, the test pattern may encompass all the pixels of a frame, i.e., the video is momentarily "blanked." The duration of such a test pattern is short enough that the subject does not notice that the video has been blanked. The blanking can occur repeatedly for a period of time, such as once every second for ten seconds, or twice every second for seconds, for example.

In another example, the same test pattern may be used in a video having a background that is still image, such as an image of tree, or an apple, or a house, or a polka dot pattern, or a polygon shape, or a cartoon character, etc., or a background that is an animated moving image, such as a segment from a Bugs Bunny cartoon, or a background that is a realistic moving image, such as an airplane taking off, or a boat floating on waves, etc.

In yet another example, the same test pattern may appear in different areas on a display screen during the video. For instance, the test pattern may appear at the center of the display screen at one point in the video, then at the top right portion of the display screen at another point in the video, then at another region of the display screen different from the top right portion at yet another point in the video.

In a further example, the size of the test pattern may be varied during the video, to see whether there is a threshold size for which a reaction occurs. For instance, the test pattern may be a circle that is 1 cm in diameter at one point in the video, then 2 cm in diameter at another point in the video, then 3 cm in diameter at yet another point in the video.

In yet another example, the test pattern may be an array of objects whose distance from each other is varied during the video, to see whether the spacing between objects has an effect on whether a reaction occurs in the subjects. For instance, the test pattern may be an array of stripes that are 1 cm apart at one point in the video, then 2 cm apart at another point in the video, then 3 cm apart at yet another point in the video.

There is no limit to the types of video backgrounds and test patterns that may be evaluated, except that the test patterns should be subliminal.

As mentioned above, a test pattern need not be embedded in a digital video but instead may be embedded in a digital still image. In this case, selected pixels of the still image are modified to correspond to the pixels of the test pattern. For example, the modified digital still image may be presented on traditional print media such as a magazine photograph, a restaurant menu, a poster, and the like.

With respect to a modified digital still image presented on traditional print media, in order for the test pattern to be subliminal the selected pixels corresponding to the test pattern cannot be grouped in such a way that they are discernible from the remainder of the digital still image. In other words, objects in the test pattern need to be sufficiently small that they cannot be consciously noticed.

With respect to a modified digital still image presented electronically, the subliminal nature of the test pattern can be achieved by controlling a duration that the test pattern appears, so that the duration is below a threshold for conscious perception, and/or by grouping the pixels of the test pattern so that objects in the test pattern are sufficiently small that they cannot be consciously noticed.

As mentioned above, a flagged test pattern or trigger pattern is re-tested at least once to confirm that the observed reaction in the subjects is attributable to viewing the flagged test pattern and not to an erroneous coincidental reaction that is not repeatable, i.e., the induced reaction cannot be reproduced when re-testing is performed. If a trigger pattern is found to induce a reaction repeatably, then the test pattern is identified as a positive or successful trigger pattern. A database or library is used to store successful trigger patterns and also to store test patterns found to be unsuccessful in triggering a reaction repeatably.

Second Embodiment

According to a second embodiment of the present invention, a system and a process are provided for evaluating whether a variation in a positive trigger pattern can affect how a subject responds when exposed to that positive trigger pattern. More specifically, for a flagged trigger pattern than has been re-tested to confirm that the reaction(s) induced by exposure to that pattern is repeatable, i.e., for a positive trigger pattern, variations are made to the positive trigger pattern and/or to the imagery (video or still) in which the positive trigger pattern is embedded to determine whether the positive trigger pattern is robust enough to induce a reaction in the subjects even if it is changed.

For example, if the positive trigger pattern is an array of black stripes, which subliminally appear in a video on a white background at a duration of 300 µs, a variation can be made to any one or a combination of the following:
  stripe color;
  stripe size (e.g., width, length);
  stripe spacing;
  number of stripes;
  stripe brightness;
  stripe location on display screen or still image;
  stripe orientation (e.g., horizontal, vertical, different angles relative to vertical);
  background color(s) and imagery;
  background brightness;
  background graphics and/or text;
  duration of appearance (e.g., 250 µs, 300 µs, 350 µs, 400 µs, 450 µs, 500 µs);
  repetition of test pattern at periodic intervals;
  repetition of test pattern at random intervals; and
  movement of stripe during the interval(s) in which it is displayed.

The variations listed above are only some of the examples of the types of variations that may be made to a positive trigger pattern, and other variations also may be made in order to determine whether there is any flexibility to vary or make changes to a positive trigger pattern and still be able to induce a reaction in subjects.

Each variation made to a positive trigger pattern is evaluated to determine whether a reaction is induced in the subjects. That is, videos are made for each variation, and each of the videos undergoes an evaluation such as that described above, as if the variation is an original test pattern that is unrelated to a previous test pattern. If a variation is found to induce a reaction repeatably in the subjects, then that variation is categorized as a positive variation and is associated with the positive trigger pattern. If no reaction is induced by a variation, or if a reaction cannot be induced repeatably in a threshold percentage of the subjects, then that variation is categorized as a negative variation and not studied further.

In another example, a positive trigger pattern is evaluated to see whether peripheral imagery, which is outside of the region containing the positive trigger pattern, can have an effect on subliminal perception. For example, if the positive trigger pattern is a red square in a background of an animated fish tank filled with cartoon turtles, then an evaluation may be made to see whether adding animated fish to the fish tank would have an effect on inducing a reaction in the subjects. The fish would move in peripheral regions surrounding the positive trigger pattern but would not enter the background region in which the positive trigger pattern is embedded. In this example, if the positive trigger pattern is associated with 40% of the subjects registering an induced reaction, then an increase to 50% with use of the modified periphery would indicate, for example, that factors other than the positive trigger pattern itself, such as movement of a peripheral object, could enhance the effectiveness of the positive trigger pattern in inducing subliminal perception. On the other hand, if a reduction is found to, for example, 30% of the subjects, it would be an indication that the positive trigger pattern should not be used in conjunction with a video showing peripheral movement when the positive trigger pattern occurs.

A positive trigger pattern and its associated positive variations are referred to herein as a group of positive patterns. A database or library is used to store each positive trigger pattern together with its associated positive variations as a group.

Third Embodiment

According to a third embodiment of the present invention, a system and a process are provided for determining the types of reactions induced in a subject exposed to a positive trigger pattern and its associated positive variations, i.e., positive patterns, and peripheral enhancements or restrictions, if any. Subjects are exposed to the positive patterns to determine how the induced reaction affects the subjects emotionally, physically, and/or behaviorally.

For example, if a positive pattern has been found to increase heart rate, then the positive pattern is evaluated to see whether the induced reaction can be used to increase alertness. For instance, if a movie when watched by subjects at 1 a.m. causes 40% of the subjects to fall asleep within the first 30 minutes and 60% of the subjects to fall asleep within the first 60 minutes, the movie is modified to include the positive pattern at the 20-minute mark, for example, to see whether exposure to the positive pattern can lead to more of the subjects being awake at the 30-minute mark of the movie, and also to see whether more of the subjects remain awake at the 60-minute mark of the movie even though the positive pattern was shown at the 20-minute mark. Optionally, instead of modifying the movie to include the positive pattern at the 20 minute mark, the movie may be modified to have the positive pattern occur, for example, every 10 minutes, with the subjects being evaluated to determine whether periodic exposure to the positive pattern is effective to increase the number (or percentage) of subjects who remain awake for the entire movie. If the positive pattern is found to increase wakefulness, the positive pattern is identified as an effective subliminal pattern for altering the emotional, physical, and/or behavioral condition of subjects exposed to the pattern. On the other hand, if the positive pattern is found to have no effect on increasing wakefulness, then this pattern may be evaluated to see whether it can be useful in another way, such as to increase endurance during a treadmill workout, or to increase concentration during mind exercises.

For instance, with respect to increasing endurance, if a workout video when watched by subjects is associated with 30% of the subjects stopping after one mile of running and 40% of the subjects stopping after two miles of running, the workout video is modified to include the positive pattern at the quarter-mile mark, for example, to see whether exposure to the positive pattern can lead to more of the subjects being able to continue running beyond one mile, and to see whether more of the subjects remain running beyond two miles even though the positive pattern was shown at the quarter-mile mark. Optionally, instead of modifying the workout video to include the positive pattern at the quarter-mile mark, the workout video may be modified to have the positive pattern occur, for example, every tenth of a mile, with the subjects being evaluated to determine whether periodic exposure to the positive pattern is effective to increase endurance. If the positive pattern is found to increase endurance, the positive pattern is identified as an effective subliminal pattern for altering the emotional, physical, and/or behavioral condition of subjects exposed to the pattern.

In another instance, with respect to increasing concentration or attention span, if an interactive video with arithmetic problems to be solved by subjects is known to result in 60% of the subjects being able to complete the problems within one hour and 75% of the subjects being able to complete the problems within two hours, the interactive video is modified to include the positive pattern at the ten-minute mark to see whether exposure to the positive pattern can lead to more of the subjects being able to complete the problems within one hour, and to see whether more of the subjects are able to complete the problems within two hours even though the positive pattern was shown at the ten-minute mark. Optionally, instead of modifying the interactive video to include the positive pattern at the ten-minute mark, the interactive video may be modified to have the positive pattern occur, for example, every five minutes, with the subjects being evaluated to determine whether periodic exposure to the positive pattern is effective to increase concentration, which is reflected in a greater percentage of the subjects being able to complete the arithmetic problems in a shorter amount of time. If the positive pattern is found to increase concentration, the positive pattern is identified as an effective subliminal pattern for altering the emotional, physical, and/or behavioral condition of subjects exposed to the pattern.

In another example, if a positive pattern is found to reduce pulse rate, then the positive pattern is evaluated to see whether the induced reaction can be used to reduce anxiety. For instance, two versions of a car-racing video game are prepared, one version in which the positive pattern is embedded and appears at least once during the game, and the other being a control version in which the positive pattern does not appear during the game. Subjects play the video game repeatedly while they are monitored for heart rate and pulse rate. The video games are randomly alternated between the embedded version with the positive pattern and the control version, and the subjects have no knowledge of which version they are playing at any particular time. Results of the heat-rate monitoring, the pulse-rate monitoring, and the game scores are evaluated to determine whether the embedded version of the game leads to an average reduction in heart rate when playing and/or an average reduction in pulse rate when playing, in comparison with the average heart rate and the average pulse rate of the subjects when playing the control version of the game. Additionally, a comparison is made of the average scores obtained by the subjects for the embedded version of the game and for the control version of the game, to see whether the positive pattern can lead to higher scores as a result of improved game-playing brought about by reduced anxiety (i.e., increase calmness). If the positive pattern is found to reduce anxiety, the positive pattern is identified as an effective subliminal pattern for altering the emotional, physical, and/or behavioral condition of subjects exposed to the pattern. On the other hand, if the positive pattern is found to have no effect on reducing anxiety when playing the video game, then this pattern may be evaluated to see whether it can be useful in another way, such as to increase sleepiness.

For instance, to evaluate the effect of the positive pattern on sleepiness, one group of subjects is shown a sleep video in which is embedded the positive pattern at least once during the video ("embedded version" herein), while a control group of subjects is shown a control version of the sleep video in which the positive pattern does not appear. Both groups of subjects watch the sleep video at bedtime while they are monitored for eyelid status (e.g., fully opened, slightly opened, closed). The subjects have no knowledge of which version of the sleep video they are watching, and are observed or monitored to determine when the eyelid status is closed, signifying sleep. A comparison is made of the average time for the subjects to fall asleep for the embedded version and for the control version of the sleep video to see whether exposure to the positive pattern is effective to induce sleep. That is, if a greater percentage of the group of subjects who watched the embedded version of the sleep video are asleep within a set time after watching the video compared with the group of subjects who watched the control version of the video, then the positive pattern is categorized as an effective subliminal pattern for altering the emotional, physical, and/or behavioral condition of subjects exposed to the pattern. A database or library is used to store each effective subliminal pattern in association with information on how it alters cognition (e.g., observed emotional, physical, and/or behavioral changes). Optionally, the database or library includes a classification of each effective subliminal pattern as a constructive/positive cognition pattern or a destructive/negative cognition pattern.

Although the examples above relate to a positive pattern embedded in a digital video, similar evaluations may be performed for a positive pattern embedded in a digital still image.

Fourth Embodiment

According to a fourth embodiment of the present invention, a system and a process are provided for utilizing a positive pattern determined to be an effective subliminal pattern (see the discussion of the third embodiment above), to affect an emotional state, a physical state, and/or a behavioral state of viewers. Unlike the subjects in the previous embodiments, who are observed or monitored under testing conditions, the viewers in the present embodiment are exposed to the effective subliminal pattern under everyday settings of "real world" conditions.

For example, if the effective subliminal pattern ("effective pattern" herein) is one that enhances alertness or wakefulness, the effective pattern may be incorporated in an automobile's HUD or Heads Up Display, which is a digital image projected onto the front windshield of the automobile. The subliminal pattern may be something that is automatically inserted into the projected digital image at periodic intervals when the automobile is in operation, or it may be something that is inserted selectively, such as only when the automobile's headlights are on. Statistics may be obtained from automobile manufacturers or governmental agencies regarding the accident rate for automobiles equipped with an HUD having the effective pattern incorporated compared with an accident rate for automobiles equipped with an HUD that does not have the effective pattern.

In another example, if the effective pattern is one that enhances alertness, the effective pattern may be incorporated in educational videos used by schools or in educational toys. For instance, a video game that is intended to promote math skills may have the subliminal pattern embedded therein to enhance the learning experience of students viewing the videos or playing with the toys. Statistics may be obtained from schools or governmental agencies regarding the math proficiency of students who use the educational videos or toys with the subliminal pattern embedded compared with students who use such educational videos or toys without the subliminal pattern.

In yet another example, if the effective pattern is one that induces calmness or reduces anxiety, the effective pattern may be incorporated in medical-office videos shown at, for example, a dentist's office, a doctor's office, or the like, to calm patients before or during a dental or medical visit. Dentists and doctors can be surveyed to see whether they notice a difference in patient demeanor when videos containing the effective pattern are shown.

In a further example, if the effective pattern is one that induces feelings of happiness, the effective pattern may be incorporated in webpages of a website to increase time spent on the website by consumers visiting the website and also to increase the likelihood that the consumers make purchases via the website. In this regard, metrics can be obtained for the average website viewing time and average sales for the website without the effective pattern being embedded in the webpages, for a period of, for example, 30 days. These metrics can be compared with metrics obtained for 30 days for the website with the effective pattern incorporated, to confirm whether the effective pattern produces beneficial consumer behavior.

The various embodiments of the present invention described above have been presented by way of example and not limitation. It will be apparent to persons skilled in the relevant art(s) that various changes in form and detail can be made therein without departing from the spirit and scope of the present invention. Thus, the present invention should not be limited by any of the above-described exemplary embodiments, but should be defined only in accordance with the following claims and their equivalents. It is also to be understood that the steps and processes recited in the claims need not be performed in the order presented.

In addition, it should be understood that the attached drawings, which highlight the functionality and advantages of the present invention, are presented as illustrative examples. The architecture of the present invention is sufficiently flexible and configurable, such that it may be utilized (and navigated) in ways other than that shown in the drawings.

What is claimed is:

1. A method to provide visual stimuli to trigger specific brain activity in a user, the method comprising:
    displaying to the user, using an electronic display, one or more images comprising one or more trigger patterns, the trigger patterns adapted to induce the specific brain activity in the user,
    wherein said one or more images are produced by displaying test images to one or more viewers while monitoring physiological characteristics of the viewers, the test images comprising test patterns, determining, based at least in part on the monitoring of the physiological characteristics of the viewers, physiological changes in the viewers induced by the test patterns during said displaying of the test images, selecting one or more of the test patterns as the trigger patterns based at least in part on said determining of the physiological changes in the viewers, and incorporating the trigger patterns resulting from said selecting into one or more base images to form said one or more images.

2. The method of claim 1, wherein the specific brain activity affects at least one of an emotional state, a physiological state, and a behavioral state of the user.

3. The method of claim 1, wherein said displaying to the user of said one or more images comprising the trigger patterns induces a reaction resulting in at least one of emotional, physiological, and behavioral changes in the user.

4. The method of claim 3, wherein the induced reaction results in at least one of enhanced alertness, reduced anxiety, reduced pain, and increased happiness.

5. The method of claim 1, further comprising receiving feedback data relating to physiological characteristics of the user monitored during said displaying to the user of said one or more images comprising the trigger patterns.

6. The method of claim 5, wherein the received feedback data relating to the physiological characteristics of the user comprises at least one of electroencephalogram (EEG), functional magnetic resonance imaging (fMRI), and magnetoencephalography (MEG) data.

7. The method of claim 5, wherein the received feedback data is obtained from a wearable device comprising one or more sensors to measure the physiological characteristics of the user.

8. The method of claim 1, wherein the electronic display comprises a screen of a personal electronic device.

9. The method of claim 8, wherein said one or more images comprising the trigger patterns are incorporated in content generated by an application running on the personal electronic device.

10. The method of claim 1, wherein said one or more images comprising the trigger patterns are displayed to the user via a wearable display.

11. The method of claim 1, wherein the test patterns comprise a first test pattern and a second test pattern which is a variation of the first test pattern.

12. The method of claim 1, wherein said determining of the changes in said viewers induced by the test patterns comprises correlating detected changes in said viewers to occurrences of the test patterns based on a timing of the test images and a timing of the detected changes in said viewers.

13. The method of claim 1, wherein the selecting one of the test patterns as the trigger pattern is based at least in part on whether the test patterns induce a change in a percentage of said viewers greater than a predetermined percentage.

14. The method of claim 1, wherein the selecting one of the test patterns as the trigger pattern is based at least in part on whether the test patterns are determined to repeatably induce a change in at least one of said viewers.

15. The method of claim 1, wherein said one or more images comprising the trigger patterns are incorporated in a video displayed to the user.

16. The method of claim 15, wherein the trigger pattern appears in the video displayed to the user for a sufficiently short duration so that the trigger pattern is not consciously noticed by the user.

17. The method of claim 15, wherein the trigger pattern encompasses all pixels of an image, of the one or more images, such that the video is blanked for a sufficiently short duration so that the user does not notice that the video has been blanked.

18. The method of claim 15, wherein the trigger pattern cannot be consciously identified by the user while viewing the one or more images.

19. The method of claim 1, wherein pixels of the trigger pattern are arranged in groups that are not discernible from pixels of a remainder of an image of the one or more images.

20. The method of claim 1, wherein pixels of the trigger pattern are arranged in groups that are sufficiently small so that the trigger pattern cannot be consciously noticed.

* * * * *